United States Patent [19]

Kimura et al.

[11] Patent Number: 5,059,532
[45] Date of Patent: Oct. 22, 1991

[54] MICROORGANISM BELONGING TO GENUS RHODOCOCCUS, AND A PROCESS FOR PRODUCING ALKENE DERIVATIVE AND UNSATURATED FATTY ACID

[75] Inventors: Yoshiharu Kimura; Shigehito Adachi; Katsutoshi Ara, all of Utsunomiya; Shigeo Inoue, Ibaraki; Kenzo Koike, Utsunomiya, all of Japan

[73] Assignee: Agency of Industrial Science & Technology, Tokyo, Japan

[21] Appl. No.: 127,119

[22] Filed: Dec. 1, 1987

[30] Foreign Application Priority Data

Feb. 18, 1987 [JP] Japan .................................. 62-33361
Feb. 18, 1987 [JP] Japan .................................. 62-33362
Feb. 18, 1987 [JP] Japan .................................. 62-33363

[51] Int. Cl.$^5$ .......................... C12P 7/04; C12P 5/02; C12P 7/62; C12N 1/20
[52] U.S. Cl. ..................................... 435/134; 435/167; 435/253.2; 435/252.1; 435/135; 435/166; 435/872; 435/249; C12N/1/20
[58] Field of Search ...................... 435/132, 135, 252.1, 435/253.2, 872, 134, 249, 822, 166, 129, 167

[56] References Cited

U.S. PATENT DOCUMENTS 3,629,072 12/1971 Casida et al. ........................ 435/872

OTHER PUBLICATIONS

Goodfellow et al, "*The Biology of the Actinomycetes*", pp. 201–228, 1983.
Shinoda et al, *Emulsions and Solubilization*, 1986, pp. 74–82.
Tsao et al ed.; Yoshida, "Aeration and Mixing in Fermentation", *Annual Reports*, pp. 1–10, 1982.
ATCC Catalogue of Bacteria, 1989, p. 186.
English Summary—"Microbial Oxidation of Higher Alkyl Compounds" by Yoshiharu Kimura (see p. 235 of the Japanese Publication dated Dec. 2, 1986, by Mr. Y. Kimura).

*Primary Examiner*—Douglas W. Robinson
*Assistant Examiner*—Irene Marx
*Attorney, Agent, or Firm*—Birch, Stewart, Kolasch & Brich

[57] ABSTRACT

Disclosed herein is a process for producing an unsaturated fatty acid or derivative thereof which comprises culturing an unsaturated fatty acid-producing microorganism belonging to the genus Rhodococcus in a medium containing a saturated fatty acid or a derivative thereof, or causing the resting cells of the microorganisms to act on a saturated fatty acid or a derivative thereof. Also disclosed herein is a process for producing an alkene or derivative thereof which comprises culturing an unsaturated hydrocarbon compound-producing microorganism belonging to the genus Rhodococcus in a medium containing an alkane or derivative thereof, or causing the resting cells of the microorganism to act on an alkane or derivative thereof.

18 Claims, 3 Drawing Sheets

MICROORGANISM BELONGING TO GENUS RHODOCOCCUS, AND A PROCESS FOR PRODUCING ALKENE DERIVATIVE AND UNSATURATED FATTY ACID

BACKGROUND OF THE INVENTION

1. Field of the Invention

The present invention relates to a new microorganism belonging to the genus Rhodococcus. More particularly, it relates to a new microorganism capable of producing an unsaturated hydrocarbon compound from a saturated hydrocarbon compound.

The present invention also relates to a new process for producing an unsaturated fatty acid and derivative thereof by the aid of said microorganism.

The present invention further relates to a new process for producing an alkene and derivative thereof by the aid of said microorganism.

2. Description of the Prior Art

Unsaturated hydrocarbon compounds such as unsaturated fatty acids and derivatives thereof having 10 to 22 carbon atoms find use as perfumes, drugs, paints, lubricants, surface active agents, and cosmetics, and also as raw materials therefor.

Heretofore, such unsaturated fatty acids and derivatives thereof have been produced by hydrolyzing animal or vegetable oils and fats or by chemical synthesis. Unfortunately, the hydrolysis of oils and fats has a disadvantage in that it yields many compounds which differ in the length of the carbon chain and the degree of saturation, and the chemical synthesis also has a shortcoming in that it needs many steps and yields mixed compounds of the cis form and the trans form.

Unsaturated fatty acids can also be produced by using a microorganism or a microorganism-derived enzyme. In this case, the hydrolysis of oils and fats is performed by the aid of lipase. However, no process is known that permits the production of unsaturated fatty acids or derivatives thereof from commercially available saturated fatty acids or derivative thereof by the aid of microorganisms.

Alkenes and derivatives thereof include many compounds useful as intermediates for the synthesis of pheromones, perfumes, and organic compounds. Heretofore, alkenes and derivatives thereof have been produced by the metathesis reaction for a halogenated monoalkene and a monoalkene catalyzed by a halogen-containing metal. A disadvantage of this process is that it is necessary to completely dehydrate and dry the raw material, catalyst, solvent, and apparatus because the catalyst is inactivated by water. Another disadvantage is that the reaction should be performed in an inert gas stream, the reaction requires complicated steps, and the reaction product is a mixture of compounds of the cis form and the trans form.

Besides the chemical synthesis, there is a known process that utilizes a microorganism (as disclosed in U.S. Pat. No. 3,629,072). Unfortunately, this process is not satisfactory as an industrial process because of its slow reaction and low yields.

In view of the above-mentioned circumstances, the present inventors carried out a research which led to the finding that a strain which had been isolated (by the present inventors) from soil on the Okinawa Main Island and mutated by irradiation with ultraviolet light has an ability to efficiently convert a saturated hydrocarbon into an unsaturated hydrocarbon compound and also has an ability to efficiently convert an alkane or a derivative thereof into an alkene or a derivative thereof. The present invention was completed on the basis of this finding.

SUMMARY OF THE INVENTION

Accordingly, it is an object of the present invention to provide a process for producing an unsaturated fatty acid or derivative thereof which comprises culturing an unsaturated fatty acid-producing microorganism belonging to the genus Rhodococcus in a medium containing a saturated fatty acid or derivative thereof, or causing the resting cells of the microorganism to act on a saturated fatty acid or derivative thereof.

It is another object of the present invention to provide a process for producing an alkene or derivative thereof which comprises culturing an unsaturated hydrocarbon compound-producing microorganism belonging to the genus Rhodococcus in a medium containing an alkane or derivative thereof, or causing the resting cells of the microorganism to act on an alkane or derivative thereof.

DETAILED DESCRIPTION OF THE INVENTION

Figure 1:
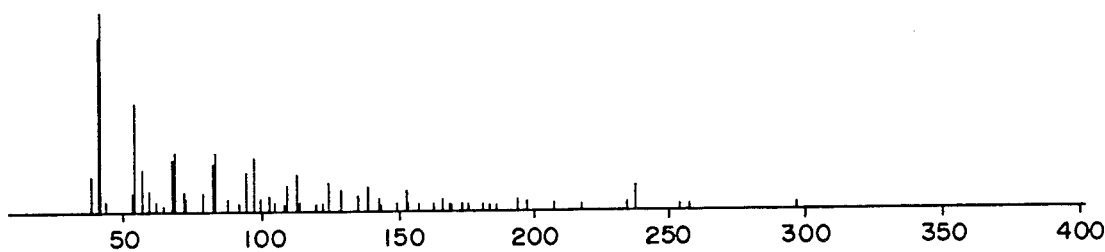
FIG. 1 is a GC-MS spectrum of propyl 6-cis-hexadecenoate.

Rhodococcus sp KSM-B-3M of the present invention has the following bacteriological characteristics:

(A) Morphology

Cells are of polymorphism; rod-like in a young culture and spherical in an old culture; and size within the approximate range of $0.5 \sim 0.8 \times 1.0 \sim 5.0$ $\mu$m.

(B) Growth on various media

On a sucrose-nitrate agar medium: poor growth, with the colony having a light flesh color and a smooth dull luster.

On a glucose-asparagine agar medium: poor growth, with the colony having a light flesh color and a smooth luster.

On a glycerin-asparagine agar medium: intermediate growth, with the colony having a milky white color and a smooth dull luster. There are smooth colonies and rough colonies.

On a starch agar medium: intermediate growth, with the colony having a milky white color and a smooth dull luster.

On a tyrosine agar medium: good growth, with the colony having a flesh color and a smooth luster. Some colonies are slimy.

On a nutrient agar medium: good growth, with the colony having a light orange color and a smooth dull luster. There are smooth colonies and rough colonies.

On a yeast-malt agar medium: good growth, with the colony having an orange color and a wavy dull luster. Some colonies are slimy.

On an oatmeal agar medium: intermediate growth, with the colony having a light orange color and a dull luster.

(C) Physiological characteristics

Conditions for growth:
  Temperature: 15°–37° C. (optimum 25°–35° C.)
  pH 5.0–9.5(optimum 6.0–8.0)
Gelatin liquefaction (on glucose-peptone-gelatin medium): negative
Hydrolysis of starch (on starch agar medium): negative
Coagulation and peptonization of skimmilk: both negative
Formation of melanine-like dye (on a tyrosine medium and a peptone-yeast-iron medium): negative (D) Assimilation of carbon sources (on Pridham-Gotreeve agar medium)
  L-arabinose+
  D-xylose+
  D-glucose+
  D-fructose+
  Sucrose+
  Inositol+
  L-rhamnose+
  Raffinose+
  D-mannitol+

(E) Chemical taxonomic characteristics
  Glycolyl test: glycolyl type
  Menaquinone system: MK-8($H_2$)

The microorganism having the above-mentioned bacteriological characteristics was recognized as a new strain belonging to the genus Rhodococcus according to Bergey's Manual of Systematic Bacteriology, Vol. 2(1986). The microorganism was designated as Rhodococcus sp KSM-B-3M, and it was deposited in the Fermentation Research Institute, Agency of Industrial Science and Technology as "Bikoken No. 9060" on Nov. 25, 1986 and as "FERM BP-1531" (according to Budapest Treaty) on Oct. 21, 1987.

The saturated fatty acid or derivative thereof used as a raw material in the present invention includes those compounds represented by

$$RCOOR_1 \quad (I)$$

where R is a straight chain or branched chain alkyl group having 9 to 21 carbon atoms; $R_1$ is a hydrogen atom, a straight chain or branched chain saturated or unsaturated hydrocarbon group having 1 to 10 carbon atoms, an alkali metal, or a group represented by

$$-N\begin{matrix} R_2 \\ R_3 \end{matrix}$$

where $R_2$ and $R_3$ are hydrogen atoms or alkyl groups having 1 to 5 carbon atoms.

Preferable among them are those in which R is a straight chain alkyl group having 9 to 21 carbon atoms.

According to the present invention, the above-mentioned saturated fatty acid or derivative thereof is converted into its corresponding unsaturated fatty acid or derivative thereof.

The process of the present invention employs a culture medium containing carbon sources, nitrogen sources, and inorganic salts necessary for the good growth of the above-mentioned microorganism. The carbon sources include carbohydrates such as glucose, fructose, sucrose, and sorbitol; organic acids such as acetic acid, citric acid, and succinic acid; and alkanes and halogenated alkanes. The nitrogen sources include sodium nitrate, potassium nitrate, yeast extract, and peptone. The inorganic salts include phosphates and magnesium sulfate. The culture medium may be incorporated with a trace amount of heavy metals.

The saturated fatty acid or derivative thereof as a raw material should preferably be added in an amount of 5 to 10% to the culture medium. For a sparingly water-soluble raw material, the culture medium should preferably be incorporated with a surface active agent such as polyoxyethylene sorbitan. The culture medium should preferably be adjusted to pH 6.5 to 8. Culturing should preferably be performed at 25° to 35° C. for 1 to 3 days while shaking or with aerated stirring.

The culture with resting cells is accomplished as follows: The microorganism is propagated on the above-mentioned culture medium. The resting cells of the microorganism isolated from the culture medium are suspended in a buffer solution such as phosphate buffer. To the resulting suspension is added an unsaturated fatty acid or derivative thereof, and the system is shaken for reaction.

As the result of culture, an unsaturated fatty acid or derivative thereof is produced in the culturing medium or the reaction mixture of resting cells. The desired unsaturated fatty acid or in derivative thereof is isolated from the culture medium or the reaction mixture of resting cells in the usual way employed for the separation and purification of organic compounds. For example, the reaction mixture is filtered to remove the culture, and the desired product is extracted from the filtrate with an organic solvent such as ethyl alcohol and chloroform. (If the desired product is a free acid, the filtrate is made acidic before extraction.) The extract is purified by column chromatography or the like to give the desired product in high purity.

The unsaturated fatty acid or derivative thereof formed in the culture medium or the reaction mixture of resting cells is identified and determined in the following manner. In the case of an unsaturated fatty acid, the solution is made alkaline with potassium hydroxide for dissolution. An aliquot of the solution is made acidic with hydrochloric acid and then extracted with chloroform. The extract is methylated with trifluoroboron-methanol complex salt. The resulting compound is analyzed and determined by gas chromatography and GC-MS. In the case of an unsaturated fatty acid ester, the solution is extracted directly with n-hexane and the extract is analyzed and determined by gas chromatography and GC-MS.

According to the process of the present invention it is possible to industrially produce an unsaturated fatty acid or derivative thereof by the aid of a specific strain belonging to the genus Rhodococcus.

The alkane or derivative thereof used as a raw material used in the present invention includes those compounds represented by

$$R-A \quad (II)$$

where R is a straight chain or branched chain hydrocarbon group having 2 or more carbon atoms, preferably 12 to 22 carbon atoms; and A is a hydrogen atom, —OH, —CN, or a group represented by

where $R_1$ and $R_2$ are hydrogen atoms or alkyl groups having 1 to 20 carbon atoms.

Preferable among the above compounds are those in which R is a straight chain hydrocarbon group having 12 to 22 carbon atoms, and A is a hydrogen atom a halogen atom (especially chlorine atom). Examples of the preferred alkane or derivative thereof include n-tetradecane, n-pentadecane, n-hexadecane, n-octadecane, n-eicosane, 1-chloro-n-tetradecane, 1-chloro-n-hexadecane, 1-chloro-n-octadecane, and 1-chloro-n-eicosane.

According to the present invention, the above-mentioned alkanes and derivatives thereof are converted into their respective alkenes and derivatives thereof such as n-tetradecene, n-pentadecene, n-hexadecene, n-octadecene, n-eicosene, 1-chloro-n-tetradecene, 1-chloro-n-hexadecene, 1-chloro-n-octadecene, and 1-chloro-no-eicosene.

The process of the present invention employs a culture medium containing carbon sources, nitrogen sources, and inorganic salts necessary for the good growth of the above-mentioned microorganism. The carbon sources include carbohydrates such as glucose, fructose, sucrose, and sorbitol; organic acids such as acetic acid, citric acid, and succinic acid; and alkanes and halogenated alkanes. The nitrogen sources include sodium nitrate, potassium nitrate, yeast extract, and peptone. The inorganic salts include phosphates and magnesium sulfate. The culture medium may be incorporated with a trace amount of heavy metals.

The alkane or derivative thereof as a raw material should preferably be added in an amount of 5 to 10% to the culture medium. For a sparingly water-soluble raw material, the culture medium should preferably be incorporated with a surface active agent such as polyoxyethylene sorbitan. The culture medium should preferably be adjusted to pH 6.5 to 8. Culturing should preferably be performed at 25° to 35° C. for 1 to 3 days while shaking or aerated stirring.

The culture with resting cells is accomplished as follows: The microorganism is propagated on the above-mentioned culture medium. The resting cells of the microorganism isolated from the culture medium are suspended in a buffer solution such as phosphate buffer. To the resulting suspension is added an alkane or derivative thereof, and the system is shaken for reaction.

As the result of culturing as set forth above, an alkene or derivative thereof is produced in the culture medium or the reaction mixture of resting cells. The desired alkene or derivative thereof is isolated from the culture medium or the reaction mixture of resting cells in the usual way employed for the separation and purification of organic compounds. For example, the reaction mixture is filtered to remove the culture, and the desired product is extracted from the filtrate with an organic solvent such as ethyl ether, n-hexane, ethyl acetate, and chloroform. The extract is purified by column chromatography or the like to give the desired product in high purity.

The alkene or derivative thereof formed in the culture medium or the reaction mixture of resting cells is identified and determined in the following manner. The solution is made alkaline with potassium hydroxide. After thorough stirring, an aliquot of the solution is extracted with n-hexane. The extract is analyzed and determined by gas chromatography and GC-MS.

According to the process of the present invention it is possible to industrially produce an alkene or derivative thereof by the aid of a specific strain belonging to the genus Rhodococcus.

EXAMPLES

The invention will be described in more detail with reference to the following examples.

EXAMPLE 1

(Microorganism)

About 0.5 g of soil sample was suspended in 10 ml of sterilized water. After thorough stirring, 0.2 ml of the resulting suspension was used to inoculate 10 ml of the liquid medium (I) in a test tube measuring 25 mm in diameter and 200 mm long. Shaking the culture was carried out at 30° C. for 4 days. The composition of the medium is shown below.

| | |
|---|---|
| n-Hexadecane | 100 g |
| $(NH_4)_2SO_4$ | 20 g |
| $KH_2PO_4$ | 20 g |
| Yeast extract | 2 g |
| $MgSO_4.7H_2O$ | 0.5 g |
| $FeSO_4.7H_2O$ | 0.01 g |
| $MnSO_4.4-6H_2O$ | 0.008 g |
| Deionized water | 1 liter |
| pH | 7 |

After multiplication by the above-mentioned culture, the culture medium was diluted with sterilized water, and the diluted solution was transferred to a nutrient agar medium (made by Eiken Kagaku Co., Ltd.). Culturing was carried out at 30° C. for 2 days. This procedure was repeated until it was confirmed with the naked eye and with a microscope that colonies on the medium are not different from one another.

The isolated strain was suspended in 0.1M phosphate buffer (pH 7.0) and the suspension was irradiated with ultraviolet light for 90 seconds. The strain was seeded onto a nutrient agar medium to give colonies. The colony was transferred to a 500-ml Sakaguchi flask containing 50 ml of liquid medium composed of glucose 2.5 g, polypeptone 17 g, polypeptone-S 3 g, $KH_2PO_4$ 2.5 g, NaCl 5 g, and deionized water 1 liter. Culturing was carried out at 30° C. for 24 hours. The centrifugally separated culture was washed with 0.25M phosphate buffer (pH 7) and then suspended in 19 ml of 0.25M phosphate buffer containing 0.5% of glucose. To the suspension was added 1 ml of n-hexadecane, followed by shaking at 30° C. for 72 hours.

The amount of n-hexadecene formed in the reaction mixture was determined by gas chromatography or other methods, and the strain that produces n-hexadecene was screened. After proper dilution with sterilized water, the n-hexadecene-producing strain was transferred to a nutrient agar medium for culture. This procedure was repeated. Each of ten colonies was inoculated onto a slant agar medium (II) of the following composition. Culturing was performed at 30° C. for 3 days. It was confirmed that the strains on the ten slant cultures were identical by observation with the naked eye and a microscope. It was also confirmed that the ten strains were identical in their character on the medium and their physiological properties.

| n-Hexadecane | 20 g |
|---|---|
| (NH₄)₂SO₄ | 20 g |
| KH₂PO₄ | 2 g |
| Yeast extract | 2 g |
| MgSO₄.7H₂O | 0.5 g |
| FeSO₄.7H₂O | 0.01 g |
| MnSO₄.4–6H₂O | 0.008 g |
| Polyoxyethylene-sorbitan monolaurate (average EO: 20 mole) | 0.05 g |
| Agar | 20 g |
| Deionized water | 1 liter |
| pH | 7 |

The thus isolated strain had the character on the medium and the physiological properties as mentioned above. The result of the test indicates that all the microorganisms of the ten cultures are of single strain.

A loopful of the strain from the pure culture on the slant medium was suspended in 2 ml of sterilized 10% glycerin solution contained in a vial for cryopreservation. After cryopreservation at −80° C. for 3 months, the suspension was restored by rapid thawing. A loopful of the suspension was placed on an agar medium for revival. The revived strain was examined for its identifying characteristics on the medium and its physiological properties under the same conditions as mentioned above. It was confirmed that the strain remained unchanged before and after cryopreservation.

The strain was subjected to the above-mentioned freezing and thawing repeatedly five times a month, and the strain was examined for its characteristics on the medium and its physiological properties under the same conditions as mentioned above. It was confirmed that the strain remained unchanged after the repeated freezing and thawing.

Example 2

(Production of unsaturated fatty acid ester)

A liquid medium was prepared from glucose 2.5 g, polypeptone 17 g, polypeptone-S 3 g, KH₂PO₄ 2.5 g, NaCl 5 g, and deionized water 1 liter. The liquid medium (50 ml) was placed in a 500-ml Sakaguchi flask, followed by steam sterilization at 120° C. for 15 minutes. The liquid medium was used for prepropagation of Rhodococcus sp KSM-B-3M. The liquid medium (0.5 ml) was inoculated into a culture medium of the same composition, followed by incubation at 30° C. for 24 hours. The centrifugally separated culture was washed with 0.25M phosphate buffer (pH 7) and then suspended in 19 ml of 0.25M phosphate buffer containing 0.5% of glucose. To the suspension was added 1 ml of propyl palmitate, followed by shaking at 26° C. for 72 hours.

Figure 2:
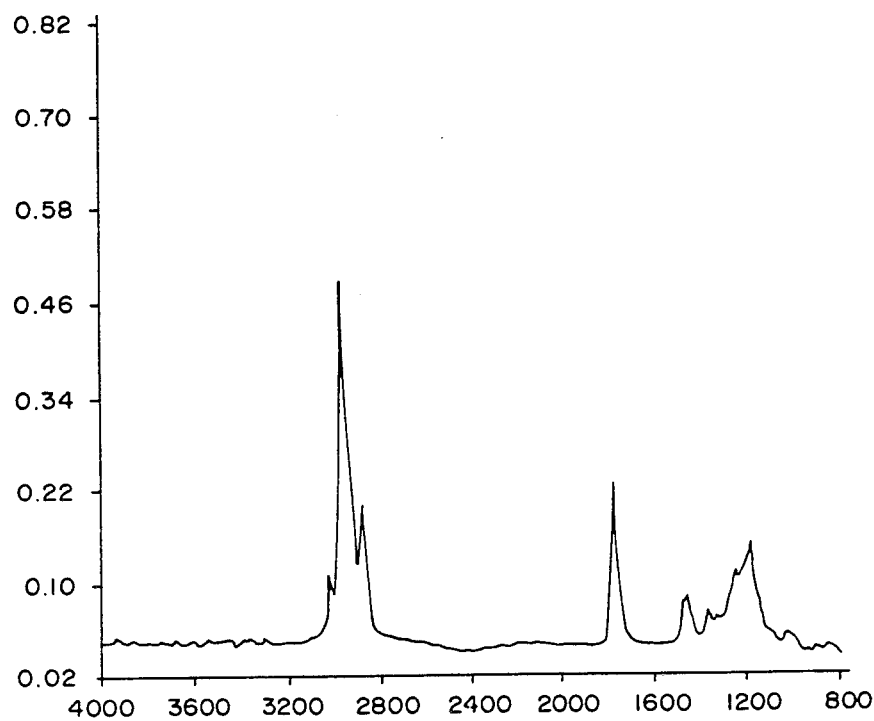
FIG. 2 is a GC-FT-IR spectrum of propyl 6-cis-hexadecenoate.
Figure 3:
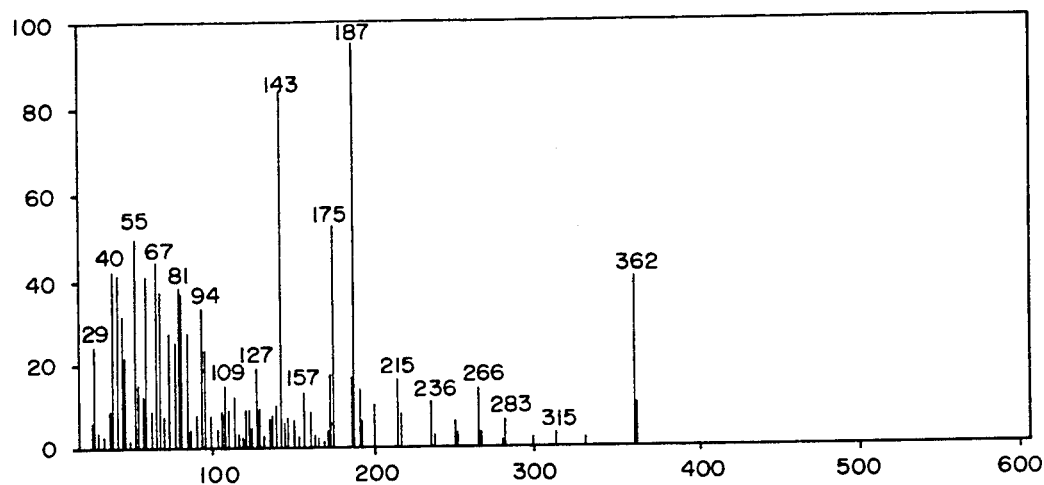
FIG. 3 is a GC-MS spectrum of dimethyl sulfide derivative of propyl 6-cis-hexadecenoate.

Propyl hexadecenoate in the reaction mixture was analyzed (by gas chromatography), identified (by GC-MS analysis, GC-FT-IR analysis, and GC-MS analysis of dimethyl sulfide derivative), and determined. It was confirmed that the reaction mixture contained 2.1 g/L of propyl 6-cis-hexadecenoate. FIG. 1 shows a GC-MS spectrum of propyl 6-cis-hexadecenoate, FIG. 2 shows a GC-FT-IR spectrum of propyl 6-cis-hexadecenoate, and FIG. 3 shows a GC-MS spectrum of the dimethyl sulfide derivative of propyl 6-cis-hexadecenoate.

Example 3

The same procedure as in Example 2 was repeated except that the propyl palmitate was replaced by sodium palmitate, methyl palmitate, or isopropyl palmitate. The unsaturated fatty acid or ester thereof in the reaction mixture was analyzed, identified, and determined in the same manner as in Example 2. The results are shown in Table 1 below.

TABLE 1

| Substrate | Product | Amount (g/L) |
|---|---|---|
| Sodium palmitate | cis-Hexadecenoic acid | 0.03 |
| Methyl palmitate | Methyl cis-hexadecenoate | 0.07 |
| Isopropyl palmitate | Isopropyl cis-hexadecenoate | 8.1 |

Example 4

A culture medium was prepared by adding 5% of isopropyl palmitate to the same culture medium as used in Example 2. The culture medium was inoculated with Rhodococcus sp KSM-B-3M, followed by incubation at 30° C. for 72 hours. After incubation, the product in the culture medium was analyzed, identified, and determined. The results indicated the presence of isopropyl cis-hexadecenoate in an amount of 0.5 g/L.

Example 5

(Production of alkene)

A liquid medium was prepared from glucose 2.5 g, polypeptone 17 g, polypeptone-S 3 g, KH₂PO₄ 2.5 g, NaCl 5 g, and deionized water 1 liter. The liquid medium (50 ml) was placed in a 500-ml Sakaguchi flask, followed by steam sterilization at 120° C. for 15 minutes. The liquid medium was used for prepropagation of Rhodococcus sp KSM-B-3M. The liquid medium (0.5 ml) was inoculated into a culture medium of the same composition, followed by incubation at 30° C. for 24 hours. The centrifugally separated culture was washed with 0.5M phosphate buffer (pH 7.0) and then suspended in 4.75 ml of 0.5M phosphate buffer containing 0.5% of glucose. To the suspension was added 0.25 ml of n-pentadecane or n-hexadecane, followed by shaking at 26° C. for 72 hours.

Monoalkenes in the reaction mixture was analyzed and identified (by gas chromatography, GC-MS analysis, GC-FT-IR analysis, and GC-MS analysis of dimethyl sulfide derivative), and determined. The results are shown in Table 2 below.

TABLE 2

| Substrate alkane | Amount of cis-mono alkane formed (g/L) | Composition of monoalkene (%) | |
|---|---|---|---|
| n-pentadecane | 6.65 | 6-cis-pentadecene | 100% |
| n-hexadecane | 7.10 | 7-cis-hexadecene | 83% |
| | | 8-cis-hexadecene | 17% |

Figure 4:
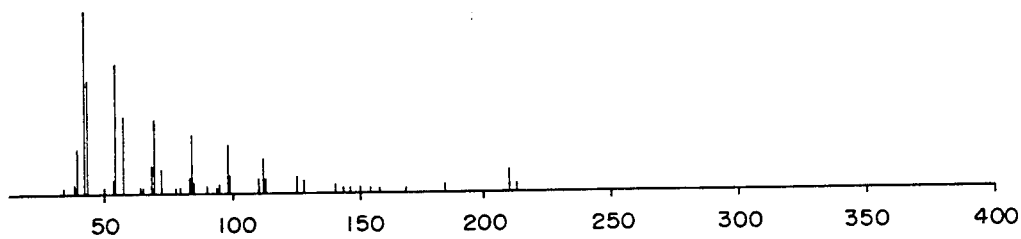
FIG. 4 is a GC-MS spectrum of 6-cis-pentadecene.
Figure 5:
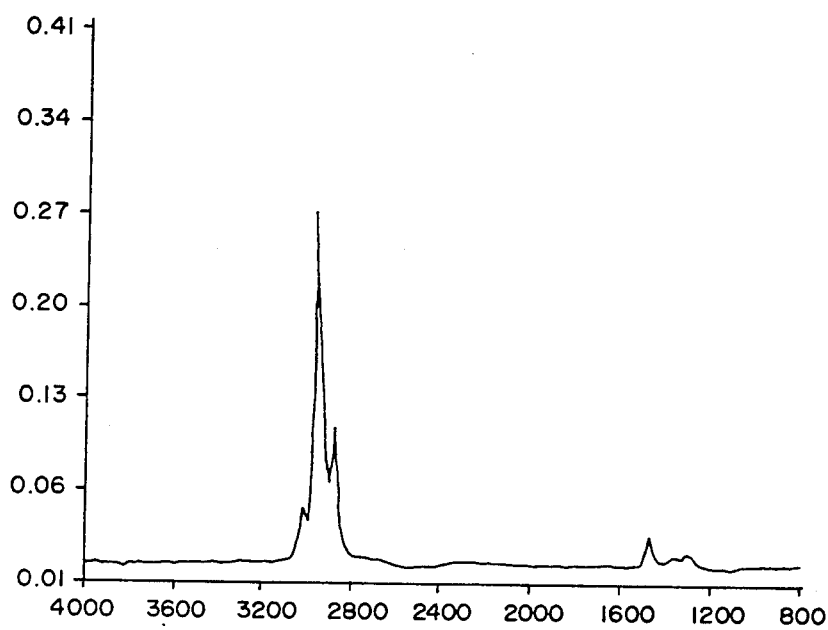
FIG. 5 is a GC-FT-IR spectrum of 6-cis-pentadecene.
Figure 6:
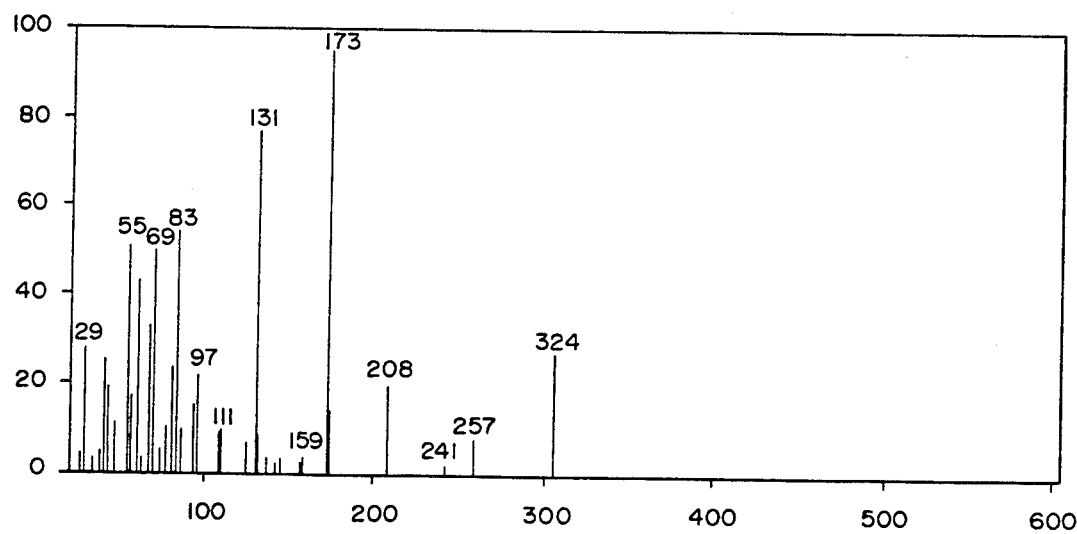
FIG. 6 is a GC-MS spectrum of dimethyl disulfide derivative of 6-cis-pentadecene.

FIG. 4 shows a GC-MS spectrum of 6-cis-pentadecene, FIG. 5 shows a GC-FT-IR spectrum of 6-cis-pentadecene, and FIG. 6 shows a GC-MS spectrum of the dimethyl sulfide derivative of 6-cis-pentadecene.

EXAMPLE 6

The same procedure as in Example 5 was repeated except that the n-heptadecane and n-hexadecane were replaced by 1-chlorohexadecane and 1-chlorooctadecane, respectively. The halogenated monoalkenes in the reaction mixture were analyzed, identified, and determined in the same manner as in Example 5. The results are shown in Table 3 below.

TABLE 3

| Substrate halogenated alkane | Amount of halogenated cis-alkane formed (g/L) | Composition of halogenated monoalkene (%) | |
|---|---|---|---|
| 1-chloro-hexadecane | 9.74 | 1-chloro-7-cis-hexadecene | 56% |
| | | 1-chloro-8-cis-hexadecene | 28% |
| | | 1-chloro-9-cis-hexadecene | 16% |
| 1-chloro-octadecane | 9.43 | 1-chloro-9-cis-octadecene | 77% |
| | | 1-chloro-8-cis-octadecene | 15% |
| | | 1-chloro-8-cis-octadecene | 8% |

EXAMPLE 7

A liquid medium (pH 7.0) was prepared from glucose 5 g, NH$_4$NO$_3$ 10 g, KH$_2$PO$_4$ 1.2 g, Na$_2$HPO$_4$ 8 g, MgSO$_4$.7H$_2$O 0.5 g, yeast extract 2 g, and deionized water 1 liter. The liquid medium (5 ml) was placed in a test tube (25 mm in diameter and 200 mm long), and 0.25 ml of n-hexadecane or 1-chloro-hexadecane was added, followed by steam sterilization at 120° C. for 15 minutes. The medium containing no (halogenated) alkane as a raw material was inoculated with Rhodococcus sp KSM-B-3M for prepropagation. The culture (0.1 ml) was then inoculated into the above-mentioned medium containing (halogenated) alkane as a raw material, followed by incubation at 30° C. for 72 hours.

The monoalkene or halogenated monoalkene in the liquid medium was analyzed, identified, and determined in the same manner as in Example 5. The results are shown in Table 4 below.

TABLE 4

| Raw material | Monoalkene formed | Amount (g/L) |
|---|---|---|
| n-Hexadecane | cis-Hexadecene | 1.16 |
| 1-chloro-hexadecane | 1-Chloro-cis-hexadecene | 0.57 |

What is claimed is:

1. A biologically pure culture of Rhodococcus sp KSM-B-3M.

2. A process for producing an unsaturated fatty acid or derivative thereof which comprises culturing the unsaturated fatty acid-producing microorganism Rhodococcus sp KSM-B-3M in a culture medium containing a saturated fatty acid or derivative thereof, or reacting the resting cells of the microorganism in a suspension of a buffer solution with a saturated fatty acid or derivative thereof, wherein the saturated fatty acid or derivative thereof is represented by RCOOR$_1$, wherein R is a straight chain alkyl group having 9 to 21 carbon atoms, R$_1$ is a hydrogen atom, a straight chain or branched chain saturated alkyl group having 1 to 10 carbon atoms, or an alkali metal and recovering said unsaturated fatty acid or derivative thereof.

3. The process as claimed in claim 2, wherein the saturated fatty acid or derivative thereof is added in an amount of 5 to 10% to the culture medium.

4. The process as claimed in claim 2, wherein the culture medium is incorporated with a surface active agent.

5. The process as claimed in claim 4, wherein the surface active agent is polyoxyethylene sorbitan.

6. The process as claimed in claim 2, wherein the pH of the culture medium is in the range of 6.5 to 8.

7. The process as claimed in claim 2, wherein culturing occurs at 25° to 35° C. for 1 to 3 days while shaking or with aerated stirring.

8. The process as claimed in claim 2, wherein the culture medium further comprises carbon sources, nitrogen sources and inorganic salts necessary for the growth of the microorganism.

9. The process as claimed in claim 8, wherein the carbon sources are selected from the group consisting of L-arabinose, D-xylose, glucose, fructose, sucrose, inositol, L-rhamnose, Raffinose, D-mannitol and sorbitol, and the nitrogen sources are selected from the group consisting of sodium nitrate, potassium nitrate, yeast extract and peptone.

10. A process for producing an alkene or derivative thereof which comprises culturing the unsaturated hydrocarbon compound-producing microorganism Rhodococcus sp KSM-B-3M in a culture medium containing an alkane or derivative thereof, or reacting the resting cells of the microorganism in a suspension of a buffer solution with an alkane or derivative thereof, wherein the alkane or derivative thereof is represented by the formula R-A, wherein R is a straight chain alkyl group having 2 to 22 carbon atoms, and A is a hydrogen atom, or a halogen atom and recovering said alkene or derivative thereof.

11. The process as claimed in claim 10, which comprises culturing Rhodococcus sp KSM-B-3M in a culture medium containing an alkane, or reacting the resting cells of the microorganism with an alkane.

12. The process as claimed in claim 10, wherein the alkane or derivative thereof is selected from the group consisting of n-tetradecane, n-pentadecane, n-hexadecane, n-octadecane, n-eicosane, 1-chloro-n-tetradecane, 1-chloro-n-hexadecane, 1-chloro-n-octadecane, and 1-chloro-n-eicosane.

13. The process as claimed in claim 10, wherein the alkane or derivative thereof is added in an amount of 5 to 10% to the culture.

14. The process as claimed in claim 10, wherein the culture medium is incorporated with a surface active agent.

15. The process as claimed in claim 10, wherein the pH of the culture medium is in the range of 6.5 to 8.

16. The process as claimed in claim 10, wherein culturing occurs at 25° to 35° C. for 1 to 3 days while shaking or with aerated stirring.

17. The process as claimed in claim 10, wherein the culture medium further comprises carbon sources, nitrogen sources and inorganic salts necessary for the growth of the microorganism.

18. The process as claimed in claim 10, wherein the resting cells are suspended in a buffer solution prior to reaction.

* * * * *